United States Patent [19]

Uesugi et al.

[11] Patent Number: 5,329,133
[45] Date of Patent: Jul. 12, 1994

[54] METHOD OF AUTOMATICALLY DETERMINING FLAWS OF AN OBJECT OF EXAMINATION

[75] Inventors: Kenji Uesugi, Yotsukaido; Michihiro Shimada, Nagoya, both of Japan

[73] Assignee: The Furukawa Electric Co., Ltd., Tokyo, Japan

[21] Appl. No.: 842,182

[22] PCT Filed: Mar. 6, 1991

[86] PCT No.: PCT/JP91/00299
§ 371 Date: Mar. 20, 1992
§ 102(e) Date: Mar. 20, 1992

[87] PCT Pub. No.: WO92/15864
PCT Pub. Date: Sep. 17, 1992

[51] Int. Cl.$^5$ ............................................. G01N 21/88
[52] U.S. Cl. .................................... 250/562; 250/572;
250/563; 356/239; 356/430
[58] Field of Search ...................... 250/572, 562, 563;
356/237, 239, 430, 431

[56] References Cited

U.S. PATENT DOCUMENTS 5,196,716 3/1993 Moriya et al. ...................... 250/572

FOREIGN PATENT DOCUMENTS 50-136089 9/1975 Japan .
50-123387 10/1975 Japan .
61-140844 6/1986 Japan .
62-173731 7/1987 Japan .
231141 7/1988 Japan .

*Primary Examiner*—Edward P. Westin
*Assistant Examiner*—T. Davenport
*Attorney, Agent, or Firm*—Jacobson, Price, Holman & Stern

[57] ABSTRACT

In a method of automatically determining flaws of an object of examination according to the invention, rays of light are transmitted through on object of examination, while adjusting the depth of observation to make it agree with the focal length of a detected flaw, go down deeper than the focal length and come up shallower than the focal length and the brightness of transmitted light for each depth of observation is converted into a corresponding electric signal. Portions of the generated signal that are found outside a predetermined range of intensity are taken out as flaw signals and the obtained flaw signals are compared with a number of binarized flaw patterns prepared from various flaws that have been detected in advance to accurately determine the type, number and size of the detected flaws.

6 Claims, 12 Drawing Sheets

FIG. 13
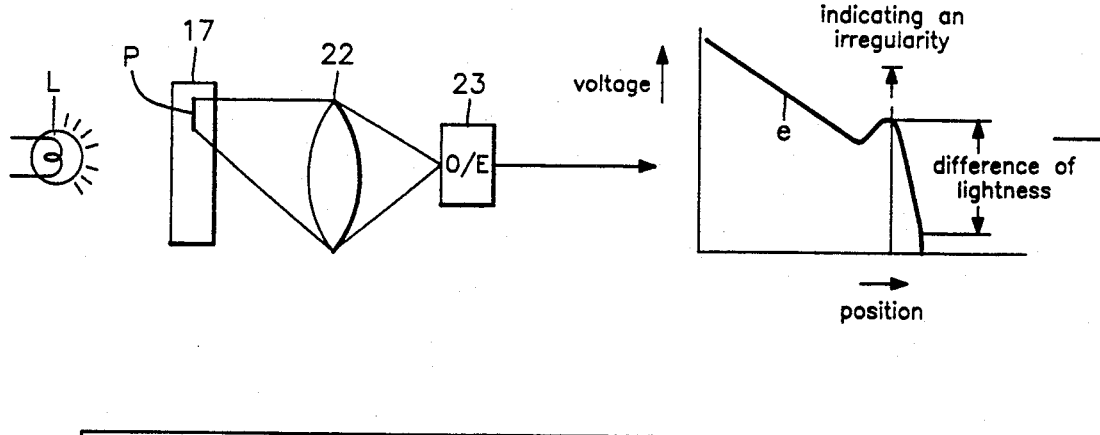
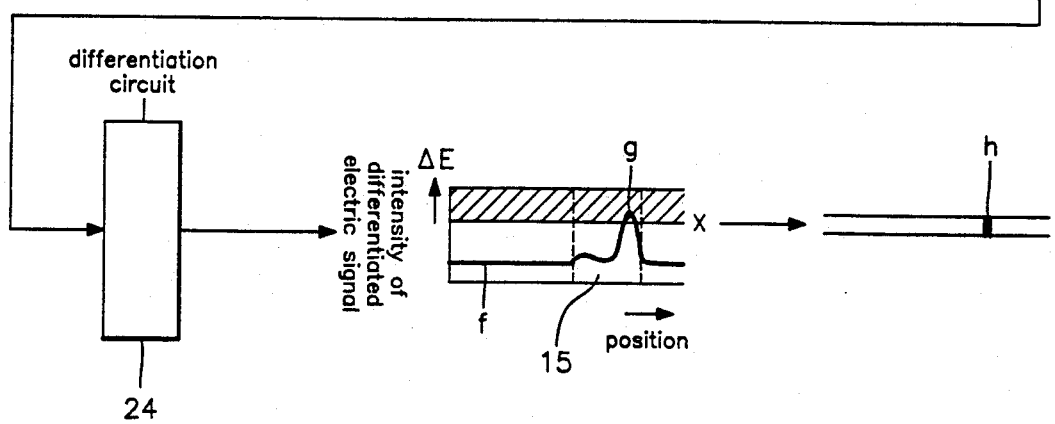
FIG. 14(a)
FIG. 14(b)
FIG. 14(c)
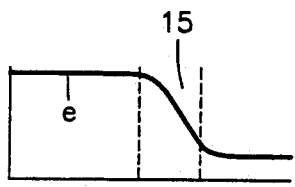
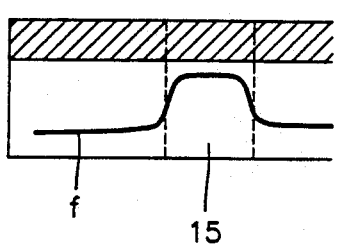
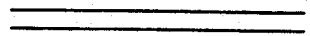

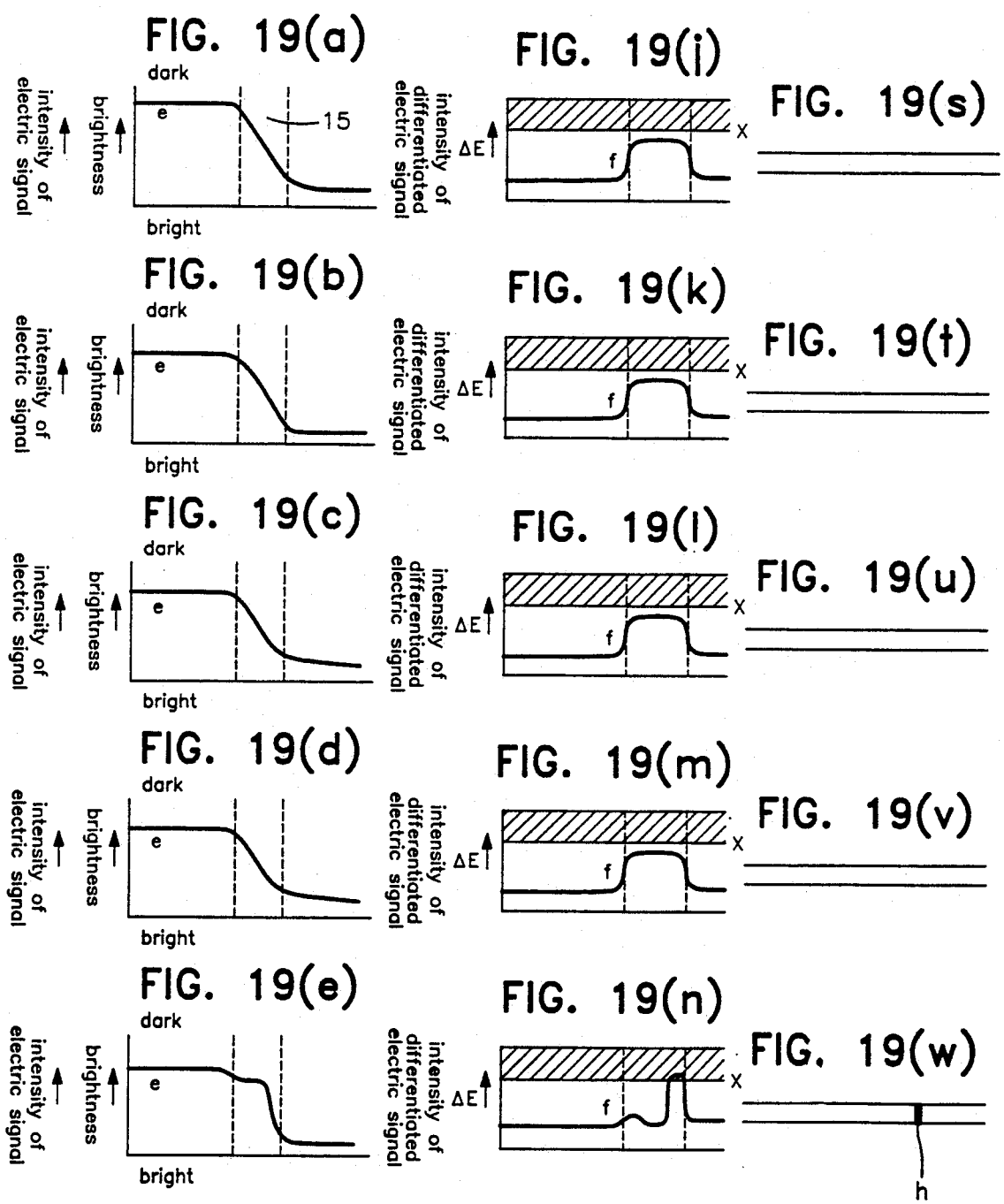

images of detected flaws

METHOD OF AUTOMATICALLY DETERMINING FLAWS OF AN OBJECT OF EXAMINATION

BACKGROUND OF THE INVENTION

1. Field of the Invention

This invention relates to a method of detecting flaws of an object of examination by using optical and electric (electronic) means and automatically determining the type and nature of each of the detected flaws.

2. Prior Art

Flaws on and/or in a product can seriously damage the performance of the product and significantly reduce its commercial value.

For instance, foreign objects contained in the insulation layers of rubber or plastic of a cable can significantly degrade the insulation breakdown characteristics of the cable.

While the probability with which foreign objects are introduced into insulation layers of rubber or plastic insulated cables has been greatly reduced with the recent development in the field of manufacture of insulated cables, there will still be a long way to go before flawless cables are produced.

Therefore, it is of vital importance to accurately analyze the insulation breakdown characteristics of each cable by examining the type, the size and the number of the flaws of the cable if it is marketed with a reliable degree of quality assurance.

In the case of an extra high voltage power cable, a minute foreign object that can be detected only by microscopic scrutiny using a microscope of a high magnification can seriously affect the insulation breakdown characteristics of the power cable if it is contained in any of its insulation layers. Therefore, a highly reliable inspection system should be established to cope with such problems, involving a large number of specimens to be examined, in order to provide an enhanced level of quality assurance for cables of this category.

The most dangerous foreign object is, of course metal debris. In order to safely eliminate metal debris from marketed cables, the type and nature of foreign objects should be determined before knowing the size and the number of the foreign objects for each type.

It is a common practice for examining the quality of a rubber or plastic insulation layer of an insulated cable to cut out a specimen having a thickness of 0.05 to 2 mm from the layer and observe the specimen through a microscope to visually determine the type, the number and the size of the flaws found in it.

Observation of a specimen proceeds in this technique proceeds in three stages: detecting flaws in the specimen, identifying each of the detected flaws by color and shape and metering the dimensions of each of the flaws (length × width × height).

Flaws in rubber or plastic insulated cables may normally grouped into three categories: ambers, black foreign objects and voids. Metal debris are regarded as black foreign objects.

When flaws are observed through a microscope that receives rays of light transmitted through the object of examination, each may take any of the following image patterns depending on the depth of observation along the center line of the microscope running through the focal point of the lens system.

Just: signifying that the depth of observation agrees with the focal length of the flaw. Under: indicating that the depth of observation is shallower than the focal length of the flaw. Over: meaning that the depth of observation is deeper than the focal length of the flaw.

These image patterns are summarized in Table 1.

Black foreign objects clearly appear black when the depth of observation is just and blurred and black when the depth of observation is under or over.

Ambers are hardly or not recognizable when the depth of observation is just because they turn totally white and do not make difference with the ambient resin color. They take on a black margin surrounding a white inside area when the depth of observation is over, whereas they are observed as totally black when the depth of observation is under.

Voids shows a black margin with the inside appearing white when the depth of observation is just, although they look just black when the depth of observation is under or over.

The effect of the above described technique of determining flaws by observation greatly depends on the skill of the operator working at the microscope and hence subject to deviations in terms of the accuracy of observation. Moreover, it is a time and labor consuming technique.

In an attempt to bypass this problem, there have been utilized automatic flaw detecting apparatus that are popularly used in other technological fields for detecting flaws of cable insulation layers.

With an apparatus of this type, flaws in a specimen of a cable insulation layer having an appropriate thickness can be automatically detected by differences in the level of brightness of the light transmitted through the specimen.

Referring to graphs (a) and (b) of FIG. 22 of the accompanying drawings, the apparatus may automatically recognize areas having a brightness lower than a predetermined threshold level X as flaws. Conversely, areas having a brightness higher than the threshold level X may be recognized as so many flaws by the apparatus.

This technique of automatic flaw detection is, however, also not without problems.

Firstly, when flaws are automatically identified by referring to the brightness of transmitted rays of light that can be higher or lower than a threshold level X, both voids that are over or under and ambers that are under appear black to the automatic flaw detector and it fails to discriminate them from each other and from black foreign objects.

Then, the net result will be incapability of meeting the requirement of classification of flaws before counting of the number and measuring the size of the flaws as in the case of microscopic observation by men.

Secondly, not only black foreign objects in the vicinity of the surface of the specimen but also scars on the surface (that can give rise to noise) can be recognized as black by the automatic detector if the threshold level X is held too high or low to enhance the sensitivity of the detector. Then, the detector will become totally powerless for flaw detection.

Thirdly, when the specimen has an uneven thickness, thin areas (bright areas) of the specimen can be recognized as white by the automatic detector.

Such white areas may be hardly discriminated from ambers which also look white when the depth of observation agrees with the focal length of the flaws.

As far as rubber or plastic insulated power cables are concerned, an irregular interface between a semi-conductive layer and an insulation layer can also provide causes of false recognition.

Some of the technological problems related to irregular interfaces and the currently available methods for determining irregularities on interfaces will be described below.

Referring to FIG. 15 of the accompanying drawings, which illustrates in cross-section a rubber or plastic insulated power cable having an inner semi-conductive layer 11, an insulation layer 14 and an outer semi-conductive layer 12, a tree (ramified crack) can develop in the insulation layer 14 if there is an irregular area in the interface 15 of the inner and/or outer semi-conductive layer 12 and the insulation layer 14 as the electric field generated in and around the cable shows a high degree of concentration there.

A flaw of this type can also lead to a degraded performance of the cable and eventually break down the insulation layer 14.

In view of the current circumstances for power cables, where rubber or plastic insulated cables and particularly bridged polyethylene insulated cables are used for extra high voltage applications involving voltages as high as 2,75 KV, cables of this type need to be carefully and microscopically scrutinized by using a large number of specimens per each cable so that any irregularities on interfaces of layers may be rigorously checked.

A known practice of microscopically examining specimens to meet rigorous requirements for high voltage applications of sheathed cables is taking specimens (such as an object of examination 17 in FIG. 16) having a thickness of approximately 0.5 mm out of a cable by means of a microtome and then visually scrutinizing them through a microscope.

Assume here that a specimen as shown in FIG. 16 is prepared by means of a microtome. Of the specimen 17 of FIG. 16, only a limited small area 18 may be observed by a single operation of microscopic examination to produce an image, for instance, as shown in FIG. 17(A).

In FIG. 17(A), the shadowed area 11 or 12 is an opaque inner or outer semi-conductive layer of the object of examination 17 and the white area 14 indicates a transmissive insulation layer, the interface 15 of the two layers being also shown as a shadowed area.

The inner or outer semi-conductive layer 11 or 12 is tapered along the interface 15 as seen from FIG. 17(C), which is a sectional view along $Y_1$—$Y_1$ line of FIG. 17(A).

An irregularity 16 found on the interface 15 is in fact part of the inner or outer semi-conductive layer 11 or 12 semispherically projecting toward the insulation layer 14 as shown in FIG. 17(C), which is a sectional view along $Y_2$—$Y_2$ line of FIG. 17(A).

Then the detected irregularity 16 may be measured for its width W, height H and surface area as illustrated in FIG. 17(A). The number of irregularities in the specimen 17 may also be counted.

The above described procedure of detecting and identifying flaws (interface irregularities) is time consuming particularly when a large number of specimens are involved because the width and height of each flaw can be very small and normally found to be around several μm.

Moreover, the reliability such a flaw checking technique may be questioned because it relies heavily on the human vision while minute irregularities of the order of micromillimeters need to be controlled to meet the current technological requirements.

There has been proposed a technique that utilizes the phenomenon that irregularities normally take the form of a semisphere as shown in FIG. 17(C) and present a shady graduation when they are magnified. In a detector realized by using this technique, a threshold value is set for detecting dark areas of irregularities and an electric signal is generated each time it detects an irregular spot.

While this technique may provide some help for flaw detection, it is not capable of identifying the boundary line of an irregular spot existing on the interface of a semi-conductive layer and an insulation layer because it can only detect the darkest areas of irregularities that exceed a preset threshold level of darkness.

In short, there have not been practically feasible methods and apparatus capable of automatically detecting irregularities on various interfaces.

SUMMARY OF THE INVENTION

It is therefore a first object of the present invention to provide a method of accurately detecting flaws in an object of examination and automatically determining the type, the number and the size of the detected flaws.

A second object of the present invention is to provide a method of automatically determining flaws which is capable of automatically detecting flaws on the interface of a semi-conductive layer and an insulation layer of a cable under examination and generating electric signals representing them.

According to an aspect of the present invention, the first object of the invention is achieved by providing a method of automatically determining flaws of an object of examination by transmitting rays of light through the object to detect flaws on and in the object on a one by one basis comprising a step of adjusting the depth of observation in three stages of making it agree with the focal length of a detected flaw, go down deeper than the focal length and come up shallower than the focal length and converting the brightness of transmitted of light into a corresponding electric signal for each stage by photoelectric conversion means, a step of selecting portions of the generated signal that are found outside a predetermined range of intensity as flaw signals and a step of comparing each of the flaw signals with a number of binarized flaw patterns prepared from various flaws that have been detected in advance.

According to another aspect of the invention, the second object of the invention is achieved by providing a method of automatically determining flaws of an object of examination taken out of an inner or outer semi-conductive layer and an adjoining insulation layer of a cable by transmitting rays of light through the object to detect flaws in the object comprising a step of converting the brightness of the light transmitted through the interface of the semi-conductive layer and the insulation layer of said object of examination into a corresponding electric signal by photoelectric conversion means and converting the obtained electric signal further into a corresponding differentiated electric signal and a step of selecting portions of the generated signal that are found outside a predetermined range of intensity as irregularity signals.

A method of automatically determining flaws of an object of examination according to the invention may find various modes of implementation as described below.

In a preferred mode of implementation of the invention, the object of examination is divided into a number of virtual layers along its height and each of the layers is examined for flaws.

In another preferred mode of implementation of the invention, each time a flaw is detected in the object of examination, it is examined to determine it type and nature by varying the depth of observation relative to it.

In still another preferred mode of implementation of the invention, the object of examination is scanned for detection of flaws and, after completion of the scanning operation, each of the detected flaws is scrutinized by varying the depth of observation along a line directed to the focal point of the flaw.

In still another preferred mode of implementation of the invention, the insulation layer of the object of examination is heated to a temperature higher than the melting point of crystal of the material constituting the insulation layer to improve its transparency and rays of light are transmitted through the interface of said insulation layer and an adjacent semi-conductive layer while the insulation layer is held transparent.

BRIEF DESCRIPTION OF THE DRAWINGS

FIG. 13 is a schematic illustration of another preferred embodiment of the method of automatically determining flaws of an object of examination according to the invention specifically designed to detect irregularities on an interface of sheath layers of a cable.

FIGS. 14a–14c are schematic illustrations showing, as possible alternatives, an electric signal, a differentiated electric signal and a binarized signals which are different from those of FIG. 13.

PREFERRED MODES OF CARRYING OUT THE INVENTION

Now, the present invention will be described in greater detail by way of preferred embodiments of the invention.

Figure 1:
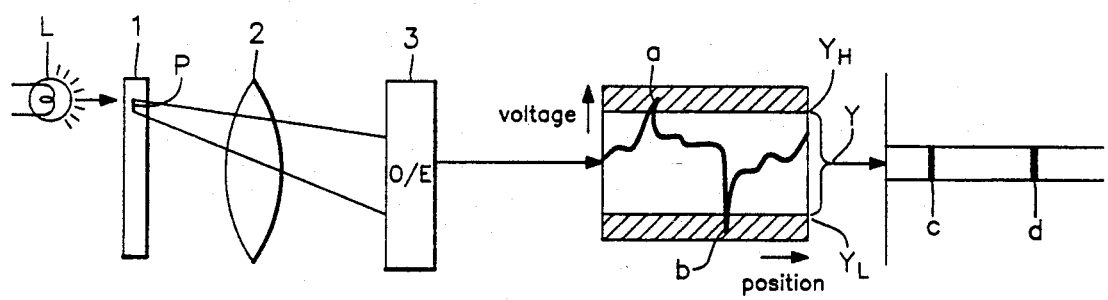
FIG. 1 is a schematic illustration of a preferred embodiment of the method of automatically determining flaws of an object of examination according to the invention.
Figure 4:
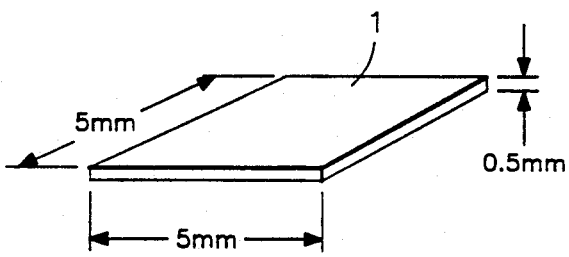
FIG. 4 is a schematic perspective view of a specimen taken from the cable of FIG. 3.

Referring to FIG. 1 showing a first preferred embodiment of the invention, rays of light are shed through a specimen 1 as shown in FIG. 4 to observe a flaw P of the specimen 1 by means of transmitted light in a microscope.

During the observation, the positional relationship between the specimen 1 and the photoelectric converter (e.g., CCD camera) 3 are modified by varying the depth of observation relative to the focal point of the flaw P to produce three different conditions where the depth of observation agrees with the focal point of the flaw P, the former comes up to a position shallower than the latter and the former goes down deeper than the latter.

The brightness of transmitted light under each of these tree conditions is converted into an electric signal for by a photoelectric converter 3 arranged at a position where an optical lens 2 forms a magnified image of the flaw.

The obtained electric signal having portions a and b that are found outside a predetermined range Y of intensity is further converted into a binarized signal comprising corresponding portions c and d representing the flaws of the specimenm which are then taken out as so many flaw signals for further use.

The pattern of each of the taken out flaw signals c and d (black or white) is compared with a number of binarized flaw patterns prepared from various flaws that have been detected in advance such as those showin in Table 1 to determine the type of the flaw.

The term "binarize a signal" in the context of this paper means to take out only portions of signals necessary for image processing of producing a visual image on the screen of a microscope and discarding the remaining unnecessary portions.

The range Y of intensity of electric signal in FIG. 1 is so set that it allows flaws of a specimen 1 to be clearly discriminated from the remaining flawless area, which will be described below.

The lower limit or threshold $Y_L$ of the range Y of intensity of electric signal is set to a level with which foreign black objects in a specimen 1 that appear black when processed for a visual image can be discrimated from dark areas of the specimen. Likewise, the upper limit or threshold $Y_H$ of the range Y is set to a level with which ambers that appear white when processed for a visual image can be discriminated from light areas of the specimen 1 (when the depth of observation agrees with the focal length of each of them) and voids can also be discernible from light areas of the specimen 1 (when the depth of observation agrees with the focal length of each of them).

Thus, portions of an electric signal that are found outside the range Y defined by the two thresholds $Y_L$ and $Y_H$ are determined to be so many flaws in the spcimen 1.

Black foreign objects, ambers and voids can be clearly identified by comparing patterns of flaw signals with binarized flaw patterns prepared from various flaws that have been detected in advance.

The total area of a specimen 1 to be observed by the embodiment of FIG. 1 can be increased to improve the accuracy of flaw detection when the specimen 1 is realized in the form of a laminate comprising a number of layers having a thickness of 5, which are examined on a one by one basis to detect flaws P in each layer.

With the embodiment of FIG. 1, each detected flaw P of a specimen 1 can be scrutinized by modifying the depth of observation for it to determine the type and nature of the flaw P.

Alternatively, it is possible with the embodiment of FIG. 1 to temprarily store data for the position of each detected flaw P of a specimen 1 and, after completion of the process of detecting flaws of the object, each of the flaws is checked for its type and nature by retrieving the data and observing it anew by modifying the depth of observation relative to the focal length.

Figure 2:
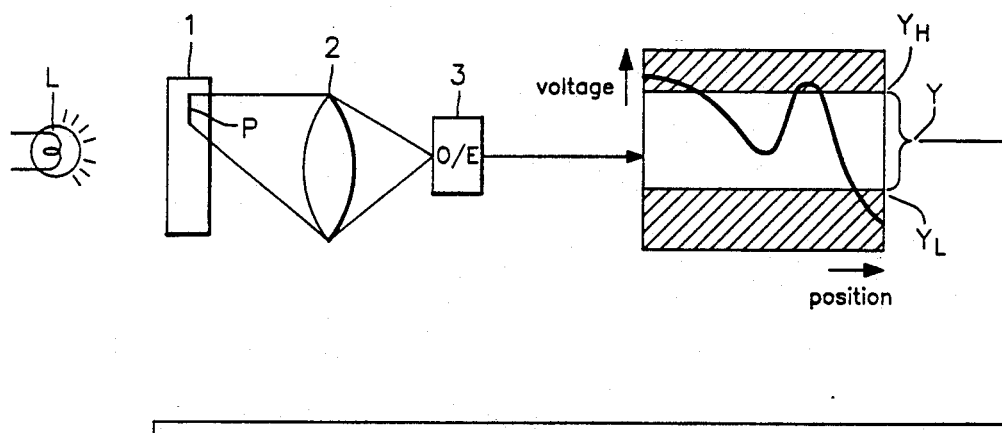
FIG. 2 is a schematic illustration of another preferred embodiment of the method of automatically determining flaws of an object of examination according to the invention.

Referring now to FIG. 2 schematically showing a second preferred embodiment of the invention, the electric signal obtained by way of a photoelectric converter 3 (e.g., CCD camera) for a specimen 1 is further converted into a differentiated electric signal by a differentiation circuit 4 and then portions e and f of the differentiated electric signal which are found out of a predetermined threshold value X of intensity of differentiated electric signal are taken out as so many flaw signagnals g and h.

The threshold value X of intensity of differentiated electric signal is so selected that flaws of a specimen 1 can be detected and identified by the difference bewteen the brightness of the picture elements of the differentiated electric signal for the specimen 1 that represent the flaws and that of the picture elements representing the areas surrounding the flaws and or the areas having only superficial scars and/or an uneven thickness.

Therefore, the second embodiment of the invention can provide a reliable method of detecting flaws in a specimen as portions of a differentiated electric signal for the specimen 1 found out of a threshold value X distinctly represent the flaws in the specimen 1.

Some of the results of exemplary experiments conducted by means of the first or second embodiments will be described.

EXAMPLE 1

Figure 3:
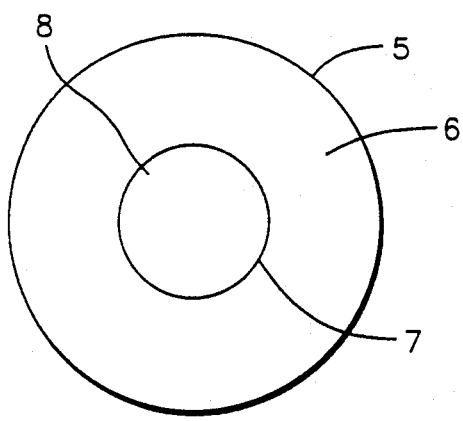
FIG. 3 is a schematic sectional view of a rubber or plastic insulated cable that can be examined for flaws by a method according to the invention.

A 66 KV bridged polyolefine insulated cable having a core conductor 8 of copper as well as an outer semi-conductive layer 5, an insulation layer and an inner semi-conductive layer 7 which were respectively 1 mm, 9 mm and 2 mm thick as shown in FIG. 3 was used.

A specimen (object of examination) which was 5 mm long, 5 mm width and 0.5 mm thick as shown in FIG. 4 was prepared from the insulation layer 6 of the cable and subjected to a process of automatic examination using the first embodiment of the invention and a microscope.

Figure 5:
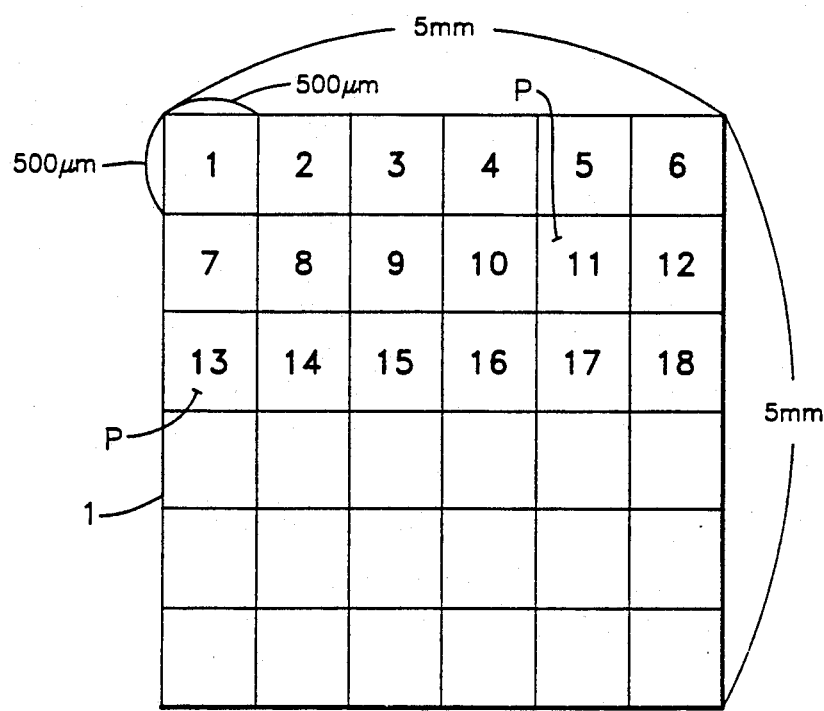
FIG. 5 is a schematic plan view of the specimen of FIG. 4.

The specimen 1 was devided into a number of sections, each having an area of approximately 500 μm that can be covered by one microscopic observation as illustrated in FIG. 5.

The sections were sequentially observed through a microscope for flaw detection.

FIG. 7 shows three different images (a), (b), and (c) obtained by microscopic observations, each revealing one or more than one flaws in the specimen.

In FIG. 7, $a_1$ is a flaw found in the image of (a), $b_1$ and $b_2$ are flaws detected in the image of (b) and $c_1$ indicates a flow observed in the image of (c).

Signals (1), (2) and (3) shown respectively in (d), (e) and (f) of FIG. 7 represent the respective levels of brightness of transmitted light passing through the dotted chain lines.

Only portions of the signals of (d), (e) and (f) in FIG. 7 that fall in zones W (white) or B (black) were recognized by the embodiment and taken out as flaw signals as they were found outside the upper and lower thresholds.

Consequently, the images of the binarized flaw signals obtained from the above process showed only black and white spots (B and W) as illustrated in (g), (h) and (i) of FIG. 7.

When the depth of observation for the image (a) of FIG. 7 was varied from shallow to deep along a line directed to the focal point of the flaw, the image was modified to appear as (a) through (e) of FIG. 8.

In FIG. 8, (a) and (b) indicate the images obtained when the depth of observation was shallow, (c) indicates the image when the depth of observation agreed with the focal length of the flaw and (d) and (e) show the images obtained when the depth of observation was deep.

Line graphs (f) through (j) of FIG. 8 respectively show lines (l) of electric signals representing the brightness of transmitted light passing through the dotted chain lines of (a) through (e).

Of the lines of (f) through (j) of FIG. 8, only portions found in zone B (black) were electrically taken out as indicants of foreign objects and reproduced in images (k) through (o) (more specifically images (l) through (n)) as black spots, which are also listed in row $a_1$ of Table 2.

Figure 7A:
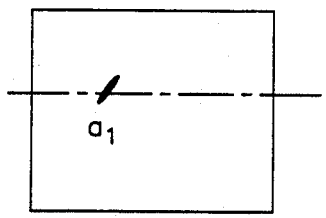
FIGS. 7a–7i are schematic illustrations showing three different images of a specimen produced on the viewing screen of a microscope, graphs showing the brightness of transmitted light for the respective images and the flaw signals obtained from the respective graphs of the brightness of transmitted of light.
Figure 7D:
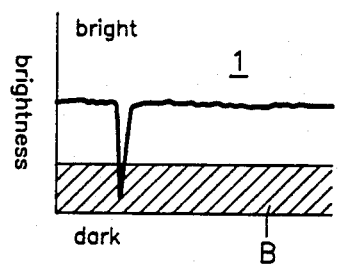
Figure 7G:
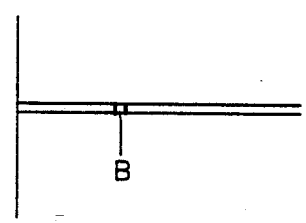

Since $a_1$ was always recognized as B (black) as shown in columns l, m and n in Table 2, the flaw $a_1$ of FIG. 7(a) was determined to be a black foreign object when compared with the image patterns of Table 1.

When the depth of observation for the image (b) of FIG. 7 was varied from shallow to deep along a line directed to the focal point of the flaws, the image was modified to appear as (a) through (e) of FIG. 9.

In FIG. 9, (a) and (b) indicate the images obtained when the depth of observation was shallow, (c) indicates the image when the depth of observation agreed with the focal length of the flaw and (d) and (e) show the images obtained when the depth of observation was deep.

Line graphs (f) through (j) of FIG. 9 respectively show lines (2) of electric signals representing the brightness of transmitted light passing through the dotted chain lines of (a) through (e).

Of the lines of (f) through (j) of FIG. 9, only portions found in zones W (white) and B (black) were electrically taken out as indicants of foreign objects and reproduced in images (k) through (o) (more specifically images (l) through (o)) white or black spots, which are also listed in rows $b_1$ and $b_2$ of Table 2.

Flaw $b_1$ was recognized in three different ways, as B as shown in columns l and m, as W and B (black margin and white inside) as shown in column n and as W as shown in column o of Table 2, while $b_2$ was recognized as B as shown in column l, as W and B as shown in column m and again as W as shown in column 2 of Table 2.

Figure 7B:
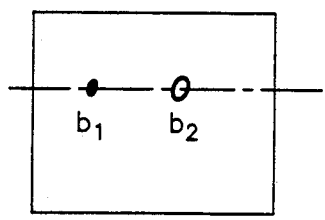
Figure 7E:
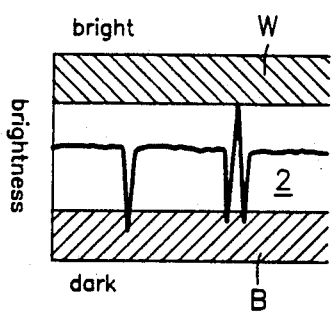
Figure 7H:
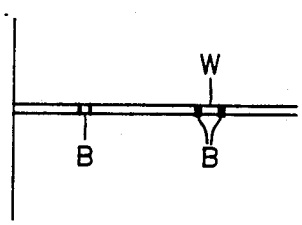

When compared with the image patterns of Table 1, both of the flaws $b_1$ and $b_2$ of FIG. 7(b) were determined to be ambers.

When the depth of observation for the image (c) of FIG. 7 was varied from shallow to deep along a line directed to the focal point of the flaw, the image was modified to appear as (a) through (e) of FIG. 10.

In FIG. 10, (a) and (b) indicate the images obtained when the depth of observation was shallow, (c) indicates the image when the depth of observation agreed with the focal length of the flaw and (d) and (e) show the images obtained when the depth of observation was deep.

Line graphs (f) through (j) of FIG. 10 respectively show lines (3) of electric signals representing the brightness of transmitted light passing through the dotted chain lines of (a) through (e).

Of the lines of (f) through (j) of FIG. 10, only portions found in zones W (white) and 2 (black) were electrically taken out as indicants of foreign objects and reproduced in images (k) through (o) (more specifically images (l) through (o)) as white and black spots, which are also listed in row $c_1$ of Table 2.

Figure 7C:
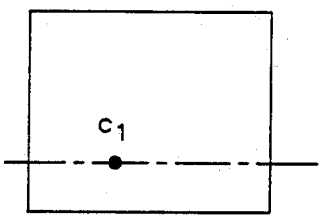
Figure 7F:
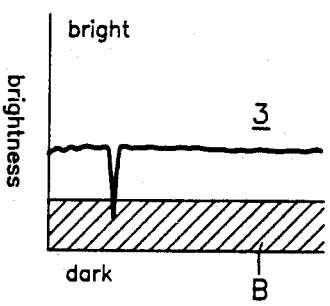
Figure 7I:
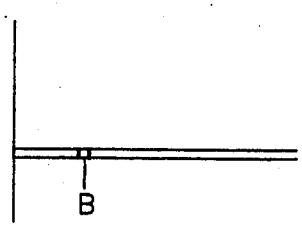
Figure 8A:
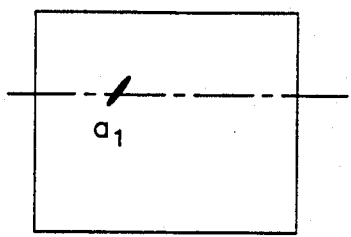
FIGS. 8a–8o are schematic illustrations showing a number of modified images of the flaw of (a) in FIG. 7 projected on a viewing screen of a microscope by varying the depth of observation, graphs showing the brightness of transmitted light for the respective images and the flaw signals obtained from the respective graphs of the brightness of transmitted light.
Figure 8F:
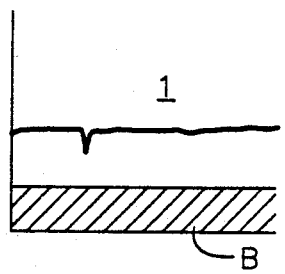
Figure 8K:
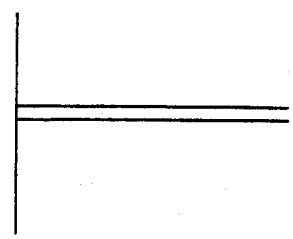
Figure 8B:
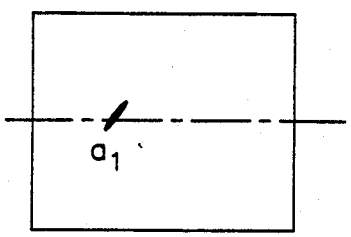
Figure 8G:
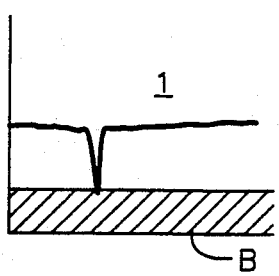
Figure 8L:
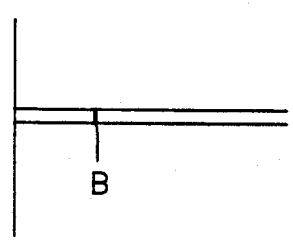
Figure 8C:
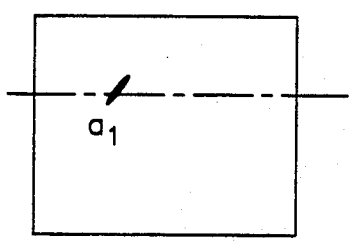
Figure 8H:
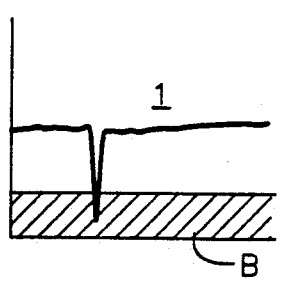
Figure 8M:
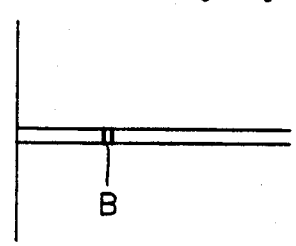
Figure 8D:
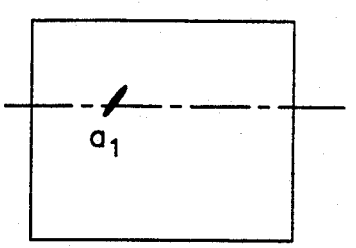
Figure 8I:
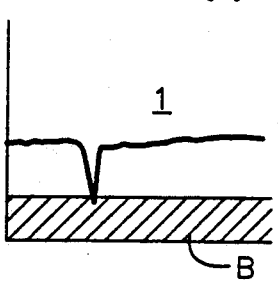
Figure 8N:
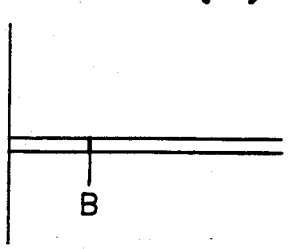
Figure 8E:
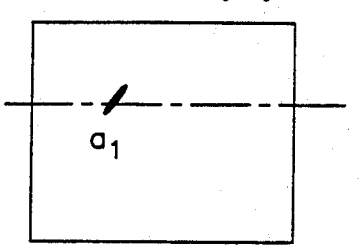
Figure 8J:
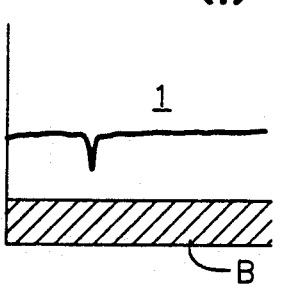
Figure 8O:
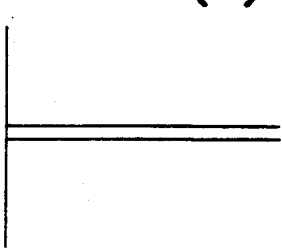
Figure 9A:
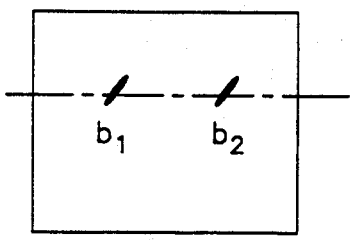
FIGS. 9a–9o are schematic illustrations similar to FIG. 8 but showing a number of modified images of the flaws of (b) of FIG. 7 projected on the viewing screen of a microscope by varying the depth of observation, graphs showing the brightness of transmitted light for the respective images and the flaw signals obtained from the respective graphs of the brightness of transmitted light.
Figure 9F:
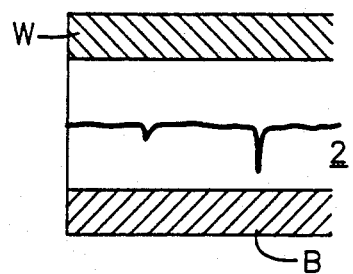
Figure 9K:
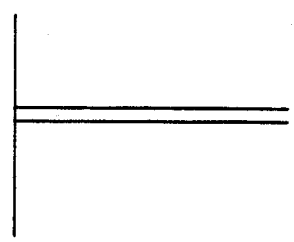
Figure 9B:
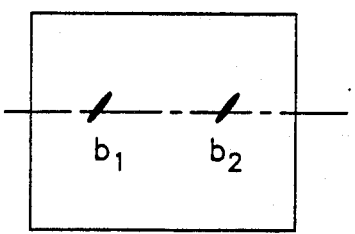
Figure 9G:
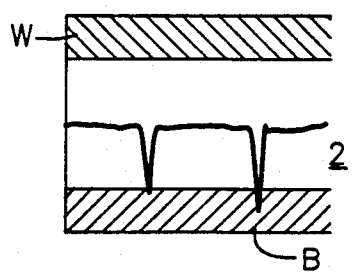
Figure 9L:
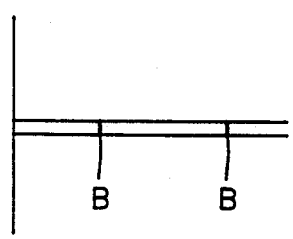
Figure 9C:
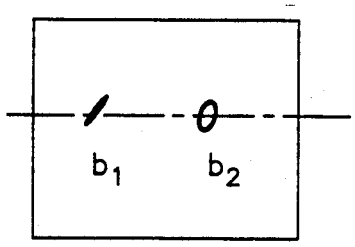
Figure 9H:
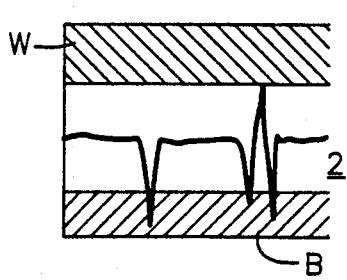
Figure 9M:
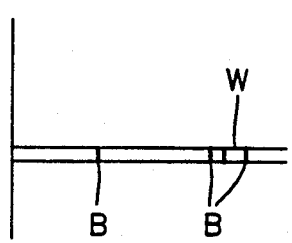
Figure 9D:
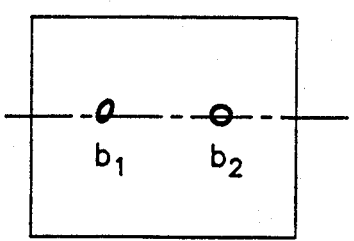
Figure 9I:
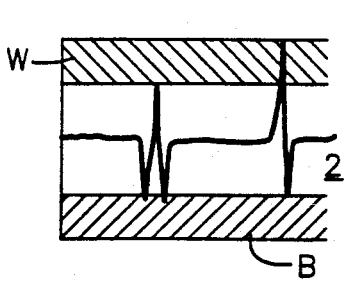
Figure 9N:
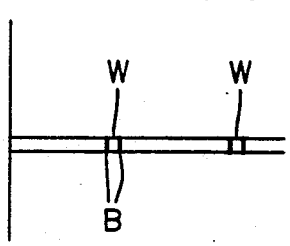
Figure 9E:
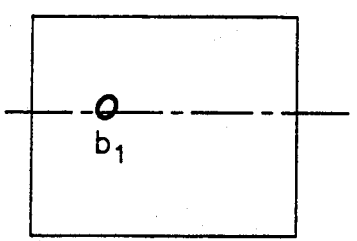
Figure 9J:
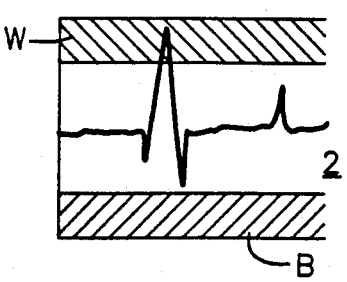
Figure 9O:
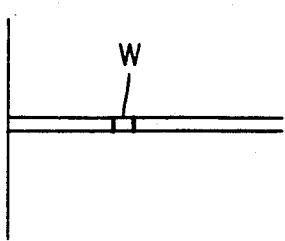
Figure 10A:
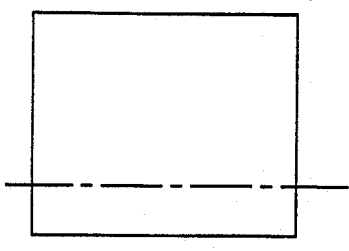
FIGS. 10a–10o are schematic illustrations similar to FIG. 8 but showing modified images of the flaw of (c) of FIG. 7 projected on the viewing screen of a microscope by varying the depth of observation, graphs showing the brightness of transmitted light for the respective images and the flaw signals obtained from the respective graphs of the brightness of transmitted light.
Figure 10F:
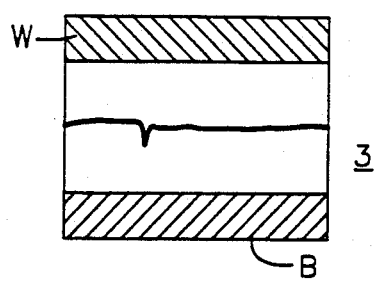
Figure 10K:
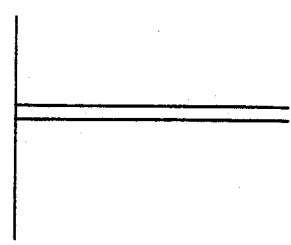
Figure 10B:
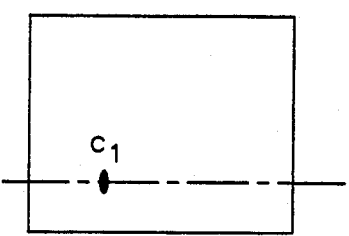
Figure 10G:
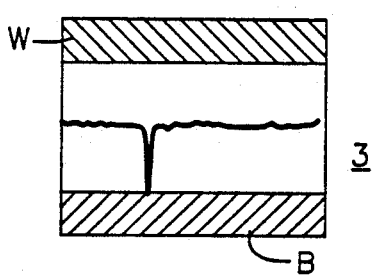
Figure 10L:
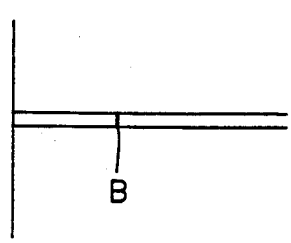
Figure 10C:
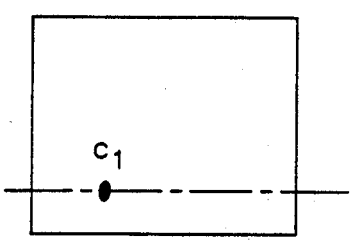
Figure 10H:
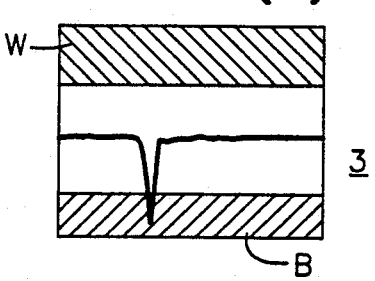
Figure 10M:
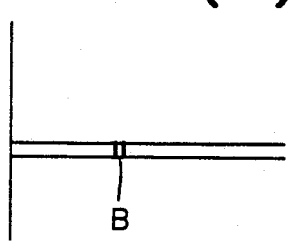
Figure 10D:
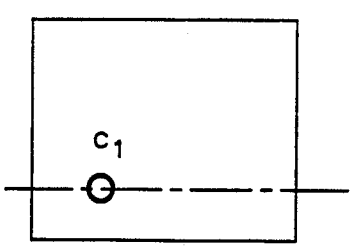
Figure 10I:
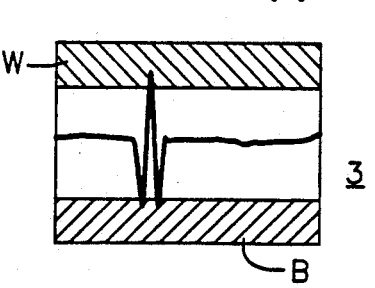
Figure 10N:
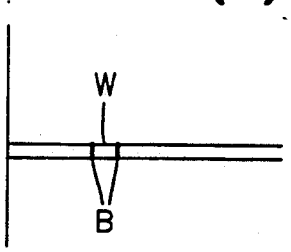
Figure 10E:
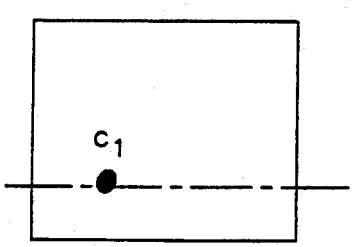
Figure 10J:
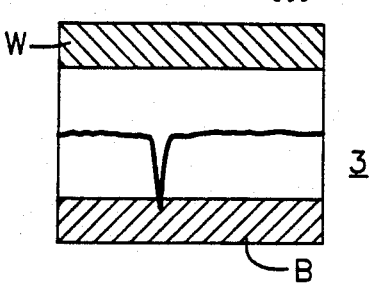
Figure 10O:
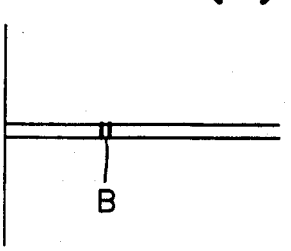
Figure 11A:
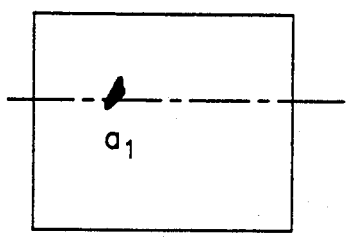
FIGS. 11a–11f are schematic illustrations similar to FIG. 7 but showing two different images of a specimen produced on the viewing screen of a microscope, graphs showing the brightness of transmitted light for the respective images and the flaw signals obtained from the respective graphs of the brightness of transmitted light.
Figure 11C:
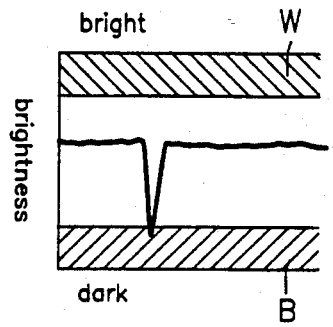
Figure 11E:
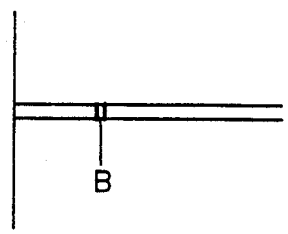
Figure 11B:
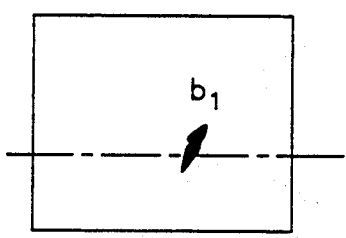
Figure 11D:
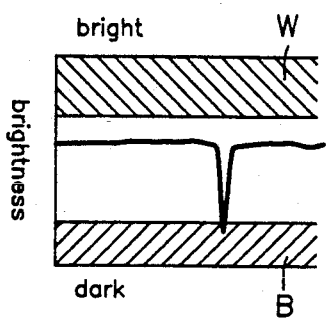
Figure 11F:
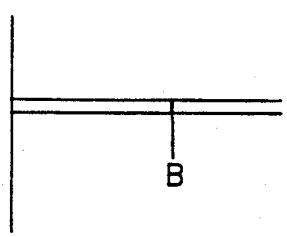

Since $c_1$ was recognized in three different ways, as B as shown in columns l and m, as both W and B as shown in column n and as B as shown in column o of Table 2, the flaw $c_1$ of FIG. 7(c) was determined to be a void when compared with the image patterns of Table 1.

Table 3 shows the final result of an operation of determining flaws conducted on the same specimen by an operator (Comparative Example 1) and that of an automatic flaw detection obtained by using a known automatic method (Comparative Example 2) as well as that of the above example listed for the purpose of comparison.

As seen from Table 3, the above example (Example 1) produced a final result of examination which is as accurate as that of Comparative Example 1, whereas the result of Comparative Example 2 was by far less accurate and totally different from those of both Example 1 and Comparative Example 1.

Therefore, it may be safely said that a method of automatically determining flaws of an object of examination according to the invention is as highly reliable as a visual method involving an operator and can produce results of examination with a remarkably high level of accuracy which any conventional methods can never achieve.

The size and number of flaws will be determined by this method for each category in a manner similar to that of a conventional method.

Figure 6:
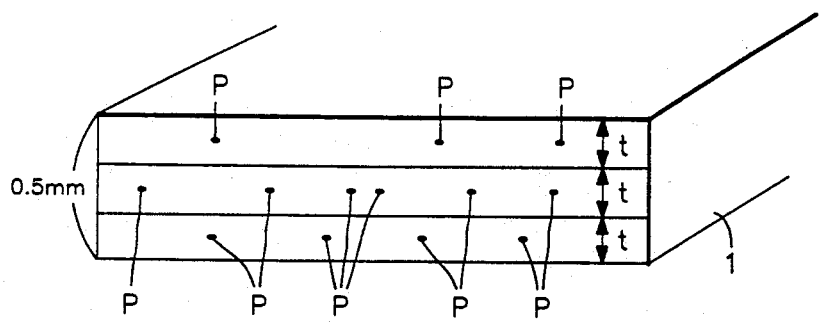
FIG. 6 is a schematic perspective partial view of a specimen shown with virtual layers.

While a specimen was divided into a number of sections, which were sequentially observed through a microscope for detection of flaws in Example 1 as shown in (a) through (c) of FIG. 7, it may be alternatively divided into virtual layers as shown in FIG. 6, which are sequentially observed for flaws on a layer by layer basis. This technique may be suited when it is desirable to observe the entire surface of a specimen at a time.

Then, each time a flaw is detected, it is subjected to a minute scrutiny to determine its type and nature by varying the depth of observation along a line directed toward the focal point of the flaw. Alternatively, the specimen 1 may be scanned for detection of flaws and each detected flaw may be registered with data representing its position so that it may be scrutinized by varying the depth of observation in a later stage.

A specimen shown in FIG. 5 was also examined for flaws and the type, the number and the size of each of the flaws were determined in three different ways—by a method according to the invention and described more specifically in Example 1, a method employed in Comparative Example 1 and a method used in Comparative Example 1. Table 4 show the result of these examinations.

EXAMPLE 2

A specimen prepared by slicing a polypropylene pellet to a thickness of 0.2 mm was examined for flaws by means of the first embodiment of the invention.

Two screen images (a) and (b) showing different flaws detected by this examination are illustrated in FIG. 11.

$a_1$ and $b_1$ indicate the respective flaws in the images (a) and (b).

(c) and (d) in FIG. 11 respectively and graphically show the levels of brightness of transmitted light along the dotted chain lines in the images (a) and (b).

As only portions of the lines of graphs (c) and (d) of FIG. 11, only portions found in low brightness zones W (white) and high brightness zones B (black) were electrically recognized by the embodiment, only those portions found in W or B zones were reproduced on the image screen of a microscope.

Consequently, images as (e) and (f) of FIG. 11 were obtained.

Thereafter, the types of the flaws of (a) and (b) were determined by varying the depth of observation from shallow to deep along a line directed toward the focal point of each flaw.

Table 5 shows the final result of the examination of Example 2 along with the result of an operation of determining flaws conducted on the same specimen by an operator (Comparative Example 3) and that of an automatic flaw detection obtained by using a known automatic method (Comparative Example 4).

As seen from Table 5, Example 2 produced a final result of examination which is as accurate as that of Comparative Example 3, whereas the result of Comparative Example 4 was by far less accurate and totally different from those of both Example 2 and Comparative Example 3.

Therefore, it may be safely said again that a method of automatically determining flaws of an object of examination according to the invention is as highly reliable as a visual method involving an operator and can produce results of examination with a remarkably high level of accuracy which any conventional methods can never achieve.

EXAMPLE 3

Foreign objects in oil were trapped by means of a filter and the specimen carrying the trapped objects was examined by the method of the invention.

Figure 12:
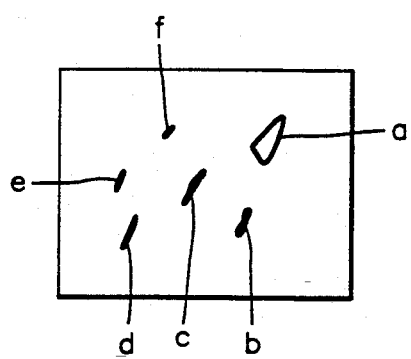
FIG. 12 is a schematic illustration showing an image of a specimen produced on the viewing screen of a microscope.

FIG. 12 shows a microscopic image where flaws of the specimen were caught.

The flaws are indicated by $a_1$, $b_1$, $c_1$, $d_1$, $e_1$ and $f_1$ in FIG. 12.

The type and nature of each of the flaws were determined by varying the depth of observation through the microscope along a line directed toward the focal point of the flaw as in the case of Example 1.

Table 6 shows the final result of the examination of Example 3 along with the result of an operation of determining flaws conducted on the same specimen by an operator (Comparative Example 5) and that of an automatic flaw detection obtained by using a known automatic method (Comparative Example 6).

As seen from Table 6, Example 3 produced a final result of examination which is as accurate as that of Comparative Example 5, whereas the result of Comparative Example 6 was by far less accurate and totally different from those of both Example 3 and Comparative Example 5.

Therefore, it may be safely said again that a method of automatically determining flaws of an object of examination according to the invention is as highly reliable as a visual method involving an operator and can produce results of examination with a remarkably high level of accuracy which any conventional methods can never achieve.

Now, another preferred embodiment of the invention will be described by referring to FIG. 13.

Figure 15:
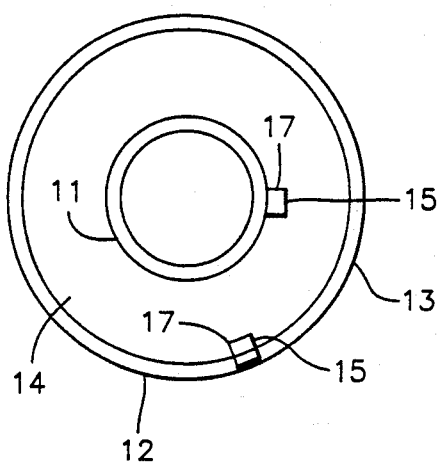
FIG. 15 is a schematic sectional view similar to FIG. 3 but showing another rubber or plastic insulated cable that can be examined for flaws by a method according to the invention.
Figure 17A:
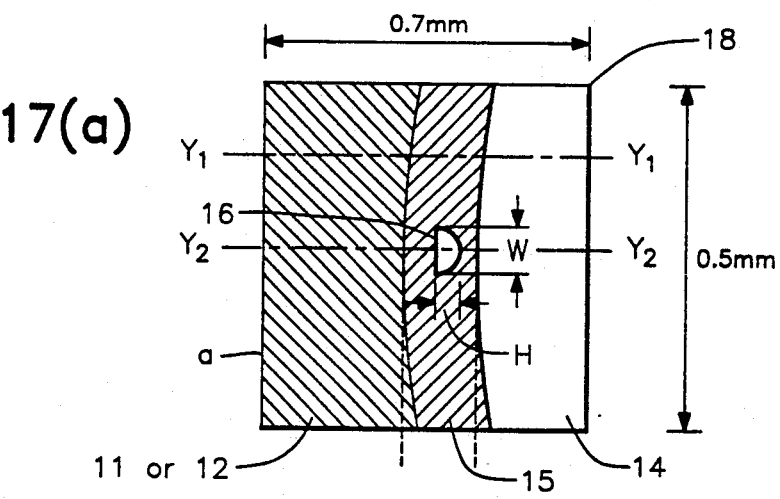
FIG. 17A is a plan view of a specimen taken from the part of FIG. 16 and produced on the screen of a microscope.
Figure 17B:
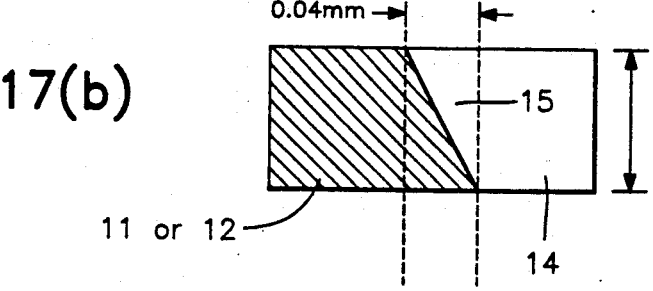
FIGS. 17B and 17C are sectional views of the specimen of FIG. 17A cut respectively along $Y_1$—$Y_1$ and $Y_2$—$Y_2$ lines.
Figure 17C:
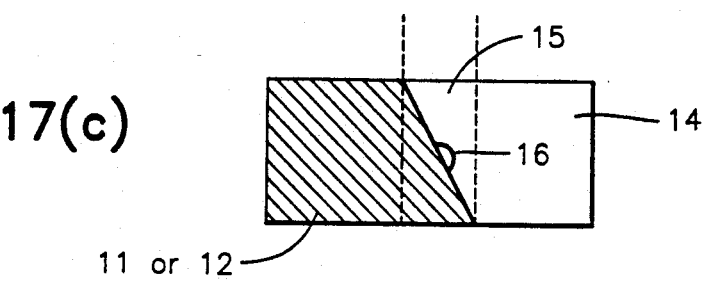

Assume that a cable 13 having a cross section as shown in FIG. 15 is examined for flaws but that the prepared specimen has a semispherical irregularity formed, conversely to the irregularity 16 of FIG. 17(C), by a small portion of the transparent insulation layer 14 projecting into the inner or outer semi-conductive layer 11 or 12 or, differently stated, by a small depression in the black semi-conductive layer 11 or 12.

For simplification, however, the flaw will be regarded as a black and projecting semispherical irregularity 16 as shown in FIG. 17(C) in the following description.

Rays of light from a light source L are transmitted through a specimen 18 taken out from a cable 13 as shown in FIG. 15 through the interface of the inner or outer semi-conductive layer 11 or 12 and the insulation layer 14 of the cable 13 and along stripes dividing the specimen to detect irregularities on the interface of the specimen 18.

After passing through the interface 14 of the semi-conductive layer 11 or 12 and the insulation layer 14, the light is caused to pass through an optical lens 22 for magnification of image and then converted into electric signals e.

Figure 18:
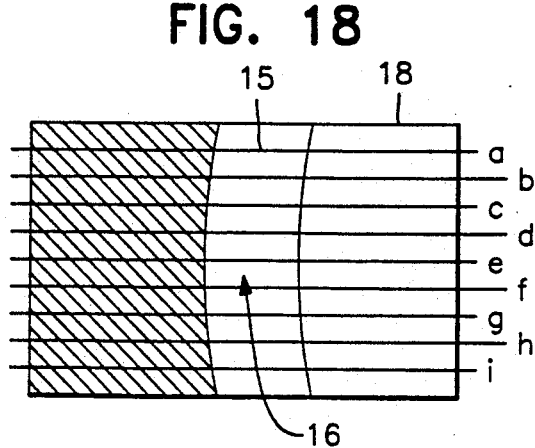
FIG. 18 is a schematic plan view of a specimen illustrating where portions of electric signals are taken out.

An area of 500 $\mu m^2$ of a specimen will be examined by a single operation of microscopic examination through the optical lens 22 of this embodiment as indicated by 18 of FIGS. 17(A) and 18. The specimen 18 is divided into stripes $a$ through $i$ as shown in FIG. 18 and the brightness of transmitted light for each of the strips $a$ through $i$ are converted into an electric signal by means of a photo-electric converter 23 to produce signals e as indicated by $1a$ through $1i$ in FIG. 19.

The electric signals e of $1a$ through $1i$ are then converted into differentiated electric signals f indicated by $2a$ through $2i$ by a differentiation circuit 24.

Figure 19F:
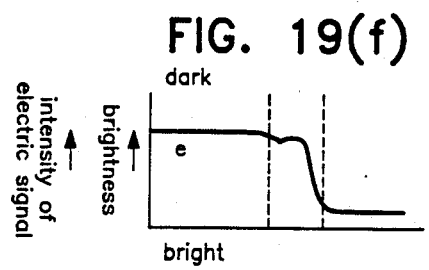
FIGS. 19a–19z and 19aa are graphic illustrations showing the electric signals of FIG. 18 and corresponding differentiated electric signals and binarized signals representing detected flaws.
Figure 19O:
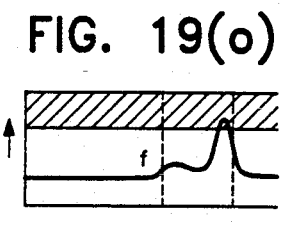
Figure 19X:
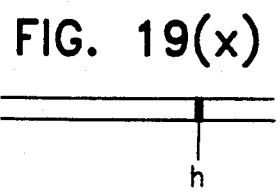
Figure 19G:
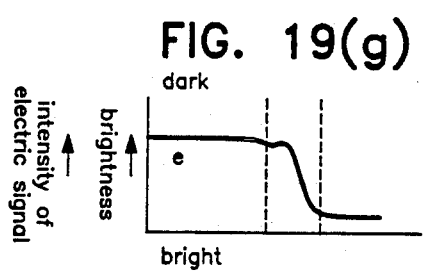
Figure 19P:
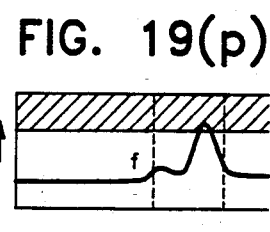
Figure 19Y:
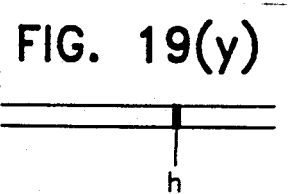
Figure 19H:
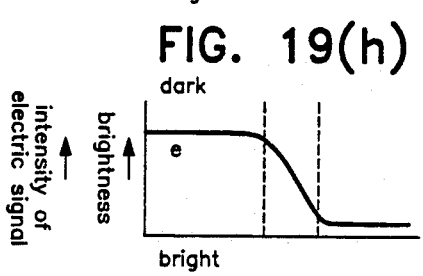
Figure 19Q:
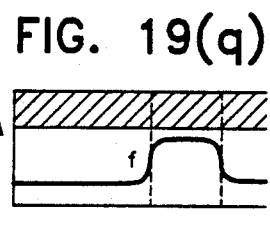
Figure 19Z:
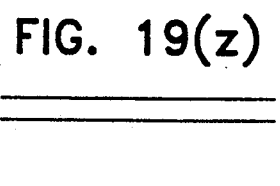
Figure 19I:
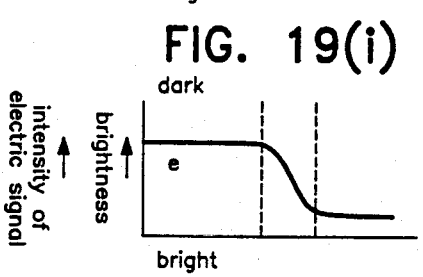
Figure 19R:
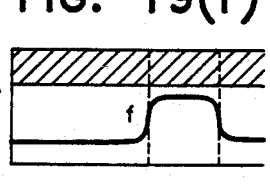
Figure 19:
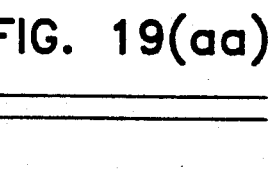

Of the differentiated electric signals f of $2a$ through $2i$, portions found outside a threshold intensity level X are detected to produce so many irregularity signals (binarized signals) h for the interface 15 as indicated by $3a$ through $3i$ in FIG. 19.

For binarization, only portions of differentiated electric signals necessary for image processing are taken out, while the remaining unnecessary portions are discarded.

Figure 20:
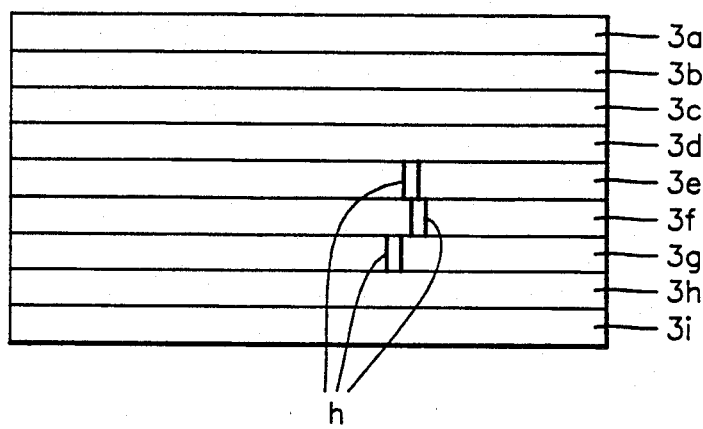
FIG. 20 is a graphic illustration showing the positional correspondence of the binarized signals of FIG. 19.

The binarized irregularity signals are then arranged on stripes that correspond to those of the specimen as shown in FIG. 20.

Figure 21:
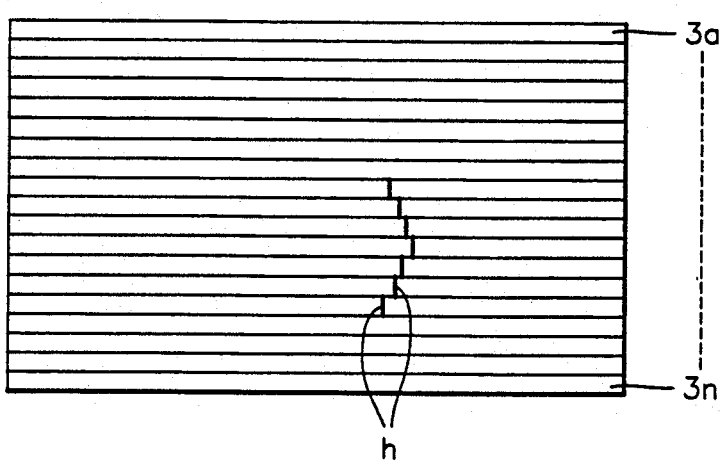
FIG. 21 is a graphic illustration of an arrangement of binarized signals similar to FIG. 20 but showing a condition where a higher level of resolution is realized.
Figure 22A:
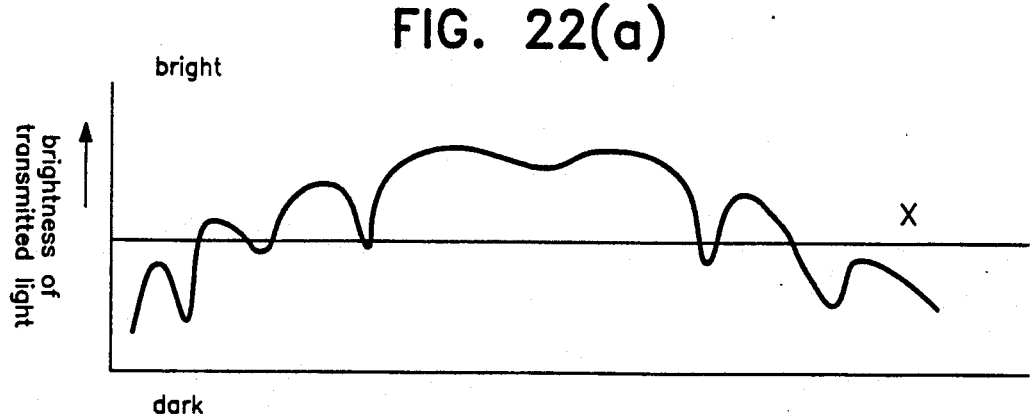
FIGS. 22a and 22b are graphs showing a typical pattern of distribution of brightness of transmitted light in a known flaw detection apparatus and images produced from the fluctuated brightness by a conventional method of automatically determining flaws of an object of examination, respectively.
Figure 22B:
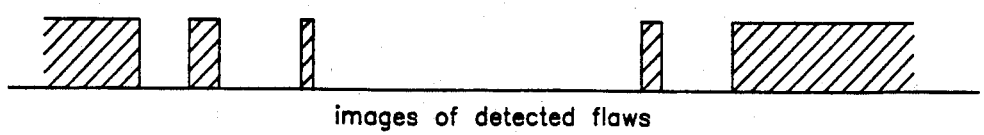

A higher resolution can be achieved for a produced image of a specimen by dividing the specimen into a greater number of stripes. A high resolution image obtained by arranging binarized signals for the specimen of FIG. 18 will show an irregularity which is very close to a semisphere as shown in FIG. 21 and therefore to the form of the original irregularity.

Thereafter, the irregularity signals are further processed to determine the width, the height and the surface area.

While the differentiated electric signal f shown in FIG. 13 has a portion g found without a threshold X of intensity, FIG. 14 shows a differentiated electric signal f which is totally confined within the threshold of intensity along with its original electric signal e and a corresponding binarized signal respectively indicated by (B), (A) and (C).

The threshold level X of intensity for differentiated electric signals should be so selected that the brightness of picture elements for irregularities and that of picture elements for surrounding areas (normal areas) show a remarkable contrast so that the difference in the brightness among picture elements for irregularities may be hardly noticeable.

An irregularity 16 can be easily detected when the interface 15 between the semi-conductive layer 11 or 12 and the insulation layer 14 is conspicuous.

If the insulation layer 14 is poorly transparent, the transparency of the insulation layer 14 may be improved by heating the object of examination 17 to a temperature higher than the melting point of crystal of the material constituting the insulation layer 14.

Figure 16:
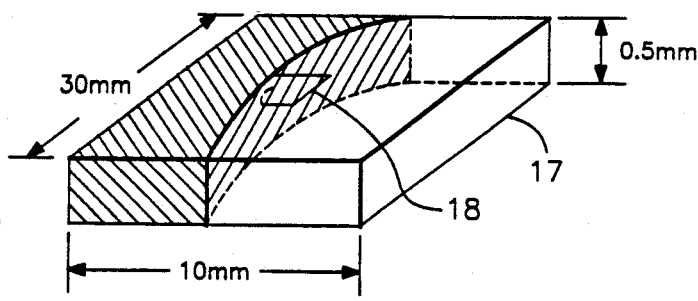
FIG. 16 is a schematic perspective view of a part of the cable of FIG. 15.

The embodiment of FIG. 16 is suitably used for detection of irregularities 16 in a specific specimen 18 of an object of examination 17.

When an object of examination 17 has to be entirely examined for detection of irregularities, the above describe technique of forming virtual layers may well be used in a following way.

The object of examination 17 is divided into a number of virtual layers having a given thickness and the multilayered object 17 is subjected to a scanning operation that proceeds from the top layer on a layer by layer basis by modifying the depth of observation for each layer so that consequently the entire object is examined for flaws.

An experiment was conducted by means of the embodiment of FIG. 13, which will be described below.

EXAMPLE 4

A specimen having a thickness of 0.5 mm (object of examination) was prepared by slicing a 66 KV bridged polyethylene insulated power cable.

The object was then examined for flaws on the interface of the inner semi-conductive layer and the insulation layer by scanning with a predetermined depth of observation along the interface.

Irregularities on the interface as small as 1 $\mu$m were detected by this scanning operation.

EXAMPLE 5

A specimen having a thickness of 2 mm was prepared from the cable of Example 4 and was examined for flaws by scanning it while heating it to a temperature higher than its melting point (120° C.) in a manner same as that of Example 4.

As a result of this operation, irregularities on the interface as small as 1 $\mu$m were detected.

Since a method of automatically determining flaws of an object of examination by transmitting rays of light through the object to detect flaws on and in the object on a one by one basis according to the invention comprises a step of adjusting the depth of observation in three stages of making it agree with the focal length of a detected flaw, go down deeper than the focal length and come up shallower than the focal length and converting the brightness of transmitted of light into a corresponding electric signal for each stage by photoelectric conversion means, a step of selecting portions of the generated signal that are found outside a predetermined range of intensity as flaw signals and a step of comparing each of the flaw signals with a number of binarized flaw patterns prepared from various flaws that have been detected in advance, it can be suitably used to automatically and accurately detect and determine black foreign objects, ambers and voids which are thee popular types of flaws can be automatically in objects of examination.

Moreover, since a method of automatically determining flaws of an object of examination taken out of an inner or outer semi-conductive layer and an adjoining insulation layer of a cable by transmitting rays of light through the object to detect flaws in the object according to the invention comprises a step of converting the brightness of the light transmitted through the interface of the semi-conductive layer and the insulation layer of said object of examination into a corresponding electric signal by photoelectric conversion means and converting the obtained electric signal further into a corresponding differentiated electric signal and a step of selecting portions of the generated signal that are found outside a predetermined range of intensity as irregularity signals, it can effectively eliminate noises due to scars on and/or an uneven thickness of the surface of the object of examination and therefore it can be advantageously used to detect any black irregularities as small as 1 $\mu$m existing on black interfaces to enhance the sensitivity and the accuracy of flaw detection.

Thus, the method of the present invention can significantly enhance the level of quality assurance of rubber or plastic insulated cables because of its high accuracy and sensitivity.

Moreover, the method of the present invention can remarkably reduce the time, labor and cost required for detection and determination of flaws since flaws are automatically detected and determined for the type, size and number by using the method of the present invention. Additionally, the method of the present invention offers a wide scope of applicability for flaw detection since it can be used for detection of flaws in any objects of examination so long as they provide a pattern of transmitted light similar to that of an insulated cable.

The accuracy and reliability of flaw detection by using the method of the present invention can be further improved when the object of examination is divided into a number of virtual layers, which is observed for flaw detection on a layer by layer basis.

Another technique of improving the accuracy and reliability of detection of irregularities on interfaces of different layers by using the method of the present invention is heating the object of examination to a given temperature to enhance the transparency of the object of examination.

TABLE 1

|  | Over | Just | Under |
| --- | --- | --- | --- |
| Foreign Object | ● | ● | ● |
| Amber | ◉ | ○ unidentifiable | ● |
| Void | ● | ◉ | ● |

TABLE 2

| | k | l | m | n | o | type of foreign object |
| --- | --- | --- | --- | --- | --- | --- |
| $a_1$ | none | B | B | B | none | black foreign object |
| $b_1$ | none | B | B | B | W | amber |
| $b_2$ | none | B | B, W | B, W | none | amber |
| $c_1$ | none | B | B | B | B | void |

TABLE 3

| foreign object | Example 1 | Comparative Example 1 | Comparative Example 2 |
| --- | --- | --- | --- |
| $a_1$ | black foreign object | black foreign object | black foreign object |
| $b_1$ | amber | amber | black foreign object |
| $b_2$ | amber | amber | amber |
| $c_1$ | void | void | black foreign object |

TABLE 4

| size μm | Example 1 | Comparative Example 1 | Comparative Example 2 |
| --- | --- | --- | --- |
| foreign black object | | | |
| 1-10 | 12 | 11 | 360 |
| 11-20 | 2 | 2 | 9 |
| 21 and above | 0 | 0 | 1 |
| void | | | |
| 1-5 | 410 | 402 | 70 |
| 6-10 | 0 | 0 | 12 |
| 11 and above | 0 | 0 | 2 |
| amber | | | |
| 1-5 | 41 | 40 | 10 |
| 6-10 | 19 | 20 | 2 |
| 11-20 | 10 | 9 | 2 |
| 21 and above | 1 | 1 | 0 |

TABLE 5

| flaw | Example 2 | Comparative Example 3 | Comparative Example 4 |
| --- | --- | --- | --- |
| $a_1$ | opaque and black foreign object | opaque and black foreign object | opaque and black foreign object |
| $b_1$ | translucent a.black foreign object | translucent a.black foreign object | opaque and black foreign object |

TABLE 6

| foreign object | Example 3 | Comparative Example 5 | Comparative Example 6 |
| --- | --- | --- | --- |
| opaque foreign object | 4 | 4 | 1 |
| translucent foreign object | 2 | 2 | 5 |

What is claimed is:

1. A method of automatically determining flaws of an object under examination by transmitting rays of light through the object to detect flaws on and in the object on a one by one basis, the method comprising the steps of:

adjusting a depth of observation in three stages of identifying the focal length of a detected flaw on the basis of light intensity of transmitted light, deeper than the focal length and shallower than the focal length and converting the intensity of transmitted light into a corresponding electric signal for each stage by photoelectric conversion means, selecting portions of the generated signal that are found outside a predetermined range of intensity as flaw signals, and comparing each of the flaw signals with a number of digitized flaw patterns prepared from various flaws that have been detected in advance.

2. A method of automatically determining flaws of an insulated cable having an inner or outer semi-conductive layer and an adjoining insulation layer comprising the steps of:

transmitting light through the cable, and converting the intensity of the light transmitted through an interface of the semi-conductive layer and the insulation layer of said cable into a corresponding electric signal by photoelectric conversion means, converting the obtained electric signal further into a corresponding differentiated electric signal, and selecting portions of the generated signal that are found outside a predetermined range of intensity as irregularity signals.

3. A method of automatically determining flaws of an object according to claim 1, wherein the object of examination is divided into a number of layers with respect to its thickness and each of the layers is examined for flaws.

4. A method of automatically determining flaws of an object according to claim 1, wherein, and further comprising the steps of determining the type and nature of the flaw by varying the depth of observation relative to it for each flaw detected in the object.

5. A method of automatically determining flaws of an object of examination according to claim 1, and comprising the step of scanning an object for detection of flaws and, upon completion of the scanning operation, varying the depth of observation along a line directed to the focal point of the flaw to scrutinize the flaw.

6. A method of automatically determining flaws of an insulated cable according to claim 2, wherein the insulation layer of the cable is heated to a temperature higher than the melting point of a rubber plastic material containing crystals to improve its transparency, and wherein light is transmitted through the interface of said insulation layer and an adjacent semi-conductive layer while the insulation layer is transparent.

* * * * *